April 25, 1972 D. F. DAYTON ET AL Plant Pat. 3,134
APPLE TREE
Filed June 17 1970
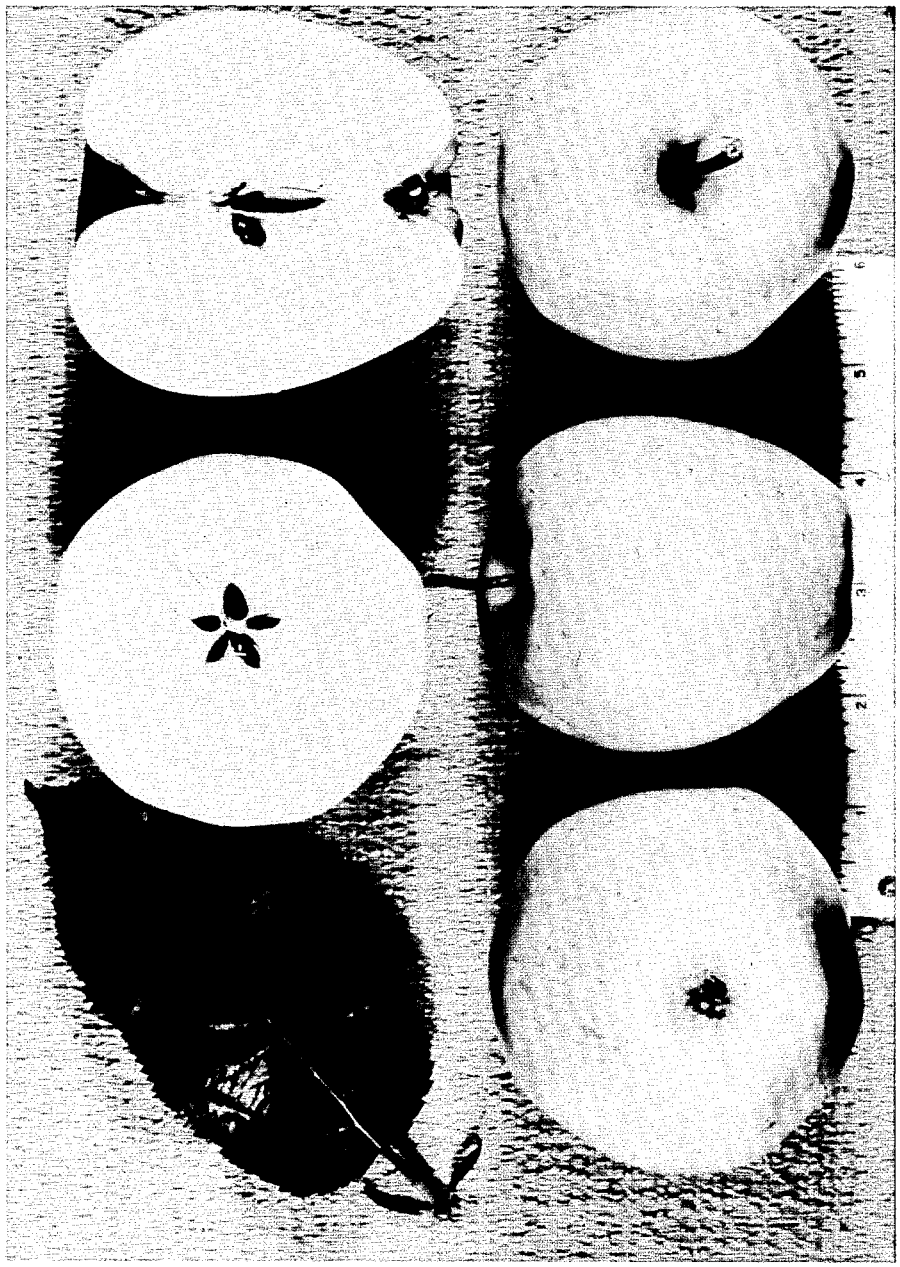
INVENTORS.
EDWIN B. WILLIAMS
JULES JANICK
FRANK H. EMERSON
DANIEL F. DAYTON
JAMES B. MOWRY
L. FREDRIC HOUGH
CATHERINE BAILEY
J. RALPH SHAY
BY: J. Mhosbitt Atty.

United States Patent Office

Plant Pat. 3,134

Patented Apr. 25, 1972

3,134
APPLE TREE

Daniel F. Dayton, Urbana, and James B. Mowry, Carbondale, Ill., L. Frederick Hough, Bloomsbury, and Catherine Bailey, Englishtown, N.J., Edwin B. Williams, Lafayette, and Jules Janick, West Lafayette, Ind., James Ralph Shay, Corvallis, Oreg., and Frank H. Emerson, Lafayette, Ind., assignors to Purdue Research Foundation, representing the State Agricultural Experiment Stations of Illinois, Indiana and New Jersey, and the Agricultural Research Service, United States Department of Agriculture

Filed June 17, 1970, Ser. No. 54,090
Int. Cl. A01h *5/03*
U.S. Cl. Plt.—34 1 Claim

A nonexclusive, irrevocable, royalty-free license in the invention herein described, throughout the world for all purposes of the United States Government, with the power to grant sub-licenses for such purposes, is hereby granted to the Government of the United States of America.

This invention is a new and distinct variety of apple tree. It was discovered by us in August 1963, in the course of our attempts to develop improved apple trees with high fruit quality and resistance to the scab disease caused by *Venturia inaequalis* (Cke.) Wint. The tree is a seedling of known parentage planted in 1958 in the S80E Breeding Orchard of the Department of Horticulture at the Illinois Agricultural Experiment Station, Urbana, Ill. In the above orchard its position was Row 22 Tree 154, having the designation 1225–100 in our breeding records.

Our present new variety of apple tree is a seedling produced from crossing the seedling 14–510 as the seed parent and the selection N.J. 123249 as the pollen parent in April 1957. This new variety carries a genetic factor ($V_f$) inherited from *Malus floribunda* 821 which causes it to be resistant to the scab disease caused by *Venturia inaequalis* (Cke.) Wint. The presence of this genetic factor has been repeatedly proven by controlled inoculation tests in the greenhouse. The complete pedigree is shown on the next page.

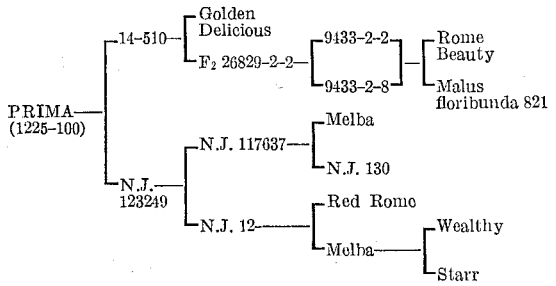

This new variety produces a vigorous and spreading tree. The tree is productive and produces annually. It is resistant to scab and shows field resistance to fireblight and apple blotch.

The tree flowers four (4) days before Golden Delicious. The apple fruits have excellent dessert quality, texture, and flavor. There is little tendency for fruit to drop before maturity. The charactristic rich flavor and crisp texture may be retained a month or more at 34° F.

After observation, the selection was asexually reproduced by grafting on seedling apple roots. The grafted material has maintained the described characteristics after propagation.

The drawing here (color photograph) shows a typical example of fruit, and foliage of our new variety. The following is a detailed description of this new variety of apple tree with the color designations according to the Horticultural Chart issued by the British Colour Council in collaboration with the Royal Horticultural Society.

*Tree*

Habit: Spreading.
Bark: Relatively smooth with prominent lenticels.

*Leaf*

Color: Dark green, healthy.
Shape: Ovate, crenate margin.
Aspect: Fairly rough upper surface, slightly pubescent on lower surface.
Size: Ratio of length to width is 2:1.
Petiole: Short, thick.

*Flower*

Pedicel: 2 cm. (¾ in.) in length.
Corolla: Petals 3.2 cm. (1¼ in.) diameter at anthesis.
Color: Solferino purple, ranging from plate 26 (tight buds) to plate 26/3 to paler in open flower.

*Fruit*

Shape: Oblate, slightly lopsided, slightly irregular.
Size: Axial diameter 6.3 to 7 cm. (2½ to 2¾ in.) transverse 7 to 7.6 cm. (2¾ to 3 in.).
Color: Undercolor uranium green (plated 63/2 to 63/3) ripening to yellow; overcolor 60 to 95 percent, cardinal red (plates 822 to 822/3); darker when overripe.
Skin: Smooth, waxy with small to medium dots, medium tough to tough, thick. No overall russeting.
Stem: 2 cm. (¾ in.) in length, medium thickness.
Cavity: Acute, deep, medium width, russetted.
Basin: Shallow to medium and broad.
Calyx: Persistent, closed, recurved.
Calyx tube: Funnel-shaped, closed.
Stamens: Marginal.
Core lines: Clasping, turbinate.
Core: Median, partly closed, small.
Carpels: Ovate, mucronate, smooth.
Seeds: Acute, not tufted.
Flesh:
*Texture.*—Medium grained, crisp, juicy.
*Quality.*—Excellent; sub-acid, rich flavor.
*Color.*—Empire yellow (plate 603/3).
*Aroma.*—Very pleasant.
Maturity season: 4 weeks before Delicious.
Keeping quality: Retains quality and texture a month or more at 34° F.
Use: Excellent dessert apple.

In particular our new variety of apple is distinguished by its resistance to scab, and its excellent dessert quality.

We claim:

1. A new and distinct variety of apple tree substantially as described and illustrated and particularly characterized by resistance to apple scab, excellent fresh fruit quality as regards rich flavor and crisp texture, and maturing approximately 4 weeks earlier than "Delicious."

No references cited.

ROBERT E. BAGWILL, Primary Examiner